United States Patent
Muraoka et al.

(10) Patent No.: US 10,242,446 B2
(45) Date of Patent: Mar. 26, 2019

(54) IMAGE PROCESSING APPARATUS AND COMPUTER-READABLE RECORDING MEDIUM

(71) Applicant: Konica Minolta, Inc., Tokyo (JP)

(72) Inventors: Shintaro Muraoka, Hachioji (JP); Tsuyoshi Kobayashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 49 days.

(21) Appl. No.: 15/591,174

(22) Filed: May 10, 2017

(65) Prior Publication Data
US 2018/0330501 A1    Nov. 15, 2018

(51) Int. Cl.
*G06K 9/00* (2006.01)
*G06T 7/00* (2017.01)
(Continued)

(52) U.S. Cl.
CPC .......... *G06T 7/0016* (2013.01); *A61B 6/5217* (2013.01); *A61B 6/5258* (2013.01);
(Continued)

(58) Field of Classification Search
CPC ....... G06T 7/0012; G06T 7/0016; G06T 7/10; G06T 7/11; G06T 7/12; G06T 5/007; G06T 5/30; G06T 5/003; G06T 5/009; G06T 5/20; G06T 5/002; G06T 5/50; G06T 5/10; G06T 11/60; G06T 11/008; G06T 2207/30061; G06T 2207/10116; G06T 2207/20128; G06T 2207/30008; G06T 2207/30172; G06T 2207/10081; G06T 2207/20016; G06T 2207/20084; G06T 2207/20216; G06T 2207/10016; G06T 2207/20192; G06T 2207/20021; G06T 2207/30004;
(Continued)

(56) References Cited

U.S. PATENT DOCUMENTS 5,982,915 A * 11/1999 Doi ................. G06T 3/0081
                                                382/130
2004/0234115 A1* 11/2004 Zijp ................. G06T 7/0016
                                                382/131
(Continued)

FOREIGN PATENT DOCUMENTS

| JP | 2003298939 A | 10/2003 |
| JP | 2009-297077 A | 12/2009 |
| JP | 2012000297 A | 1/2012 |

OTHER PUBLICATIONS

Official Notification of Refusal dated Jan. 23, 2018 from the corresponding Japanese Application No. JP 2014-206125 and English translation.

*Primary Examiner* — Jose L Couso
(74) *Attorney, Agent, or Firm* — Lucas & Mercanti, LLP

(57) ABSTRACT

An image processing apparatus includes a structure reducing unit which reduces spatial signal change by a predetermined structure in an X-ray image group in which a plurality of images obtained by capturing a same site of a same subject a plurality of times using an X-ray are aligned in a time series. The structure reducing unit reduces the spatial signal change by the predetermined structure in each image of the X-ray image group using information of an image different from the image of the X-ray image group being processed.

18 Claims, 8 Drawing Sheets

(51) Int. Cl.
*G06T 7/11* (2017.01)
*G06T 11/60* (2006.01)
*A61B 6/00* (2006.01)

(52) U.S. Cl.
CPC ............... *G06T 7/11* (2017.01); *G06T 11/60* (2013.01); *G06T 2207/10116* (2013.01); *G06T 2207/30008* (2013.01)

(58) Field of Classification Search
CPC . G06T 2207/10088; G06T 2207/20182; G06T 2210/41; G06T 2211/412; G06T 2211/404; G06T 2211/424; A61B 6/5217; A61B 6/5258; A61B 6/00; A61B 6/484–6/486; A61B 6/5247; A61B 6/469; A61B 6/02; A61B 6/463; A61B 8/4416; A61B 2090/376; G06K 7/1099; A61N 5/1037; A61N 2005/1061
See application file for complete search history.

(56) References Cited

U.S. PATENT DOCUMENTS

| | | | |
|---|---|---|---|
| 2005/0100208 A1 | 5/2005 | Suzuki et al. | |
| 2005/0111718 A1* | 5/2005 | MacMahon | A61B 6/463 382/130 |
| 2007/0133736 A1* | 6/2007 | Chen | A61B 6/00 378/5 |
| 2010/0067772 A1* | 3/2010 | Kitamura | A61B 6/482 382/132 |
| 2012/0130238 A1* | 5/2012 | Muraoka | A61B 6/4233 600/436 |
| 2013/0156267 A1* | 6/2013 | Muraoka | A61B 6/5217 382/103 |
| 2014/0079309 A1* | 3/2014 | Huo | G06T 7/0012 382/132 |
| 2015/0254841 A1* | 9/2015 | Fujiwara | G06T 7/0012 378/62 |
| 2015/0310625 A1* | 10/2015 | Shimamura | A61B 6/4233 382/132 |

* cited by examiner

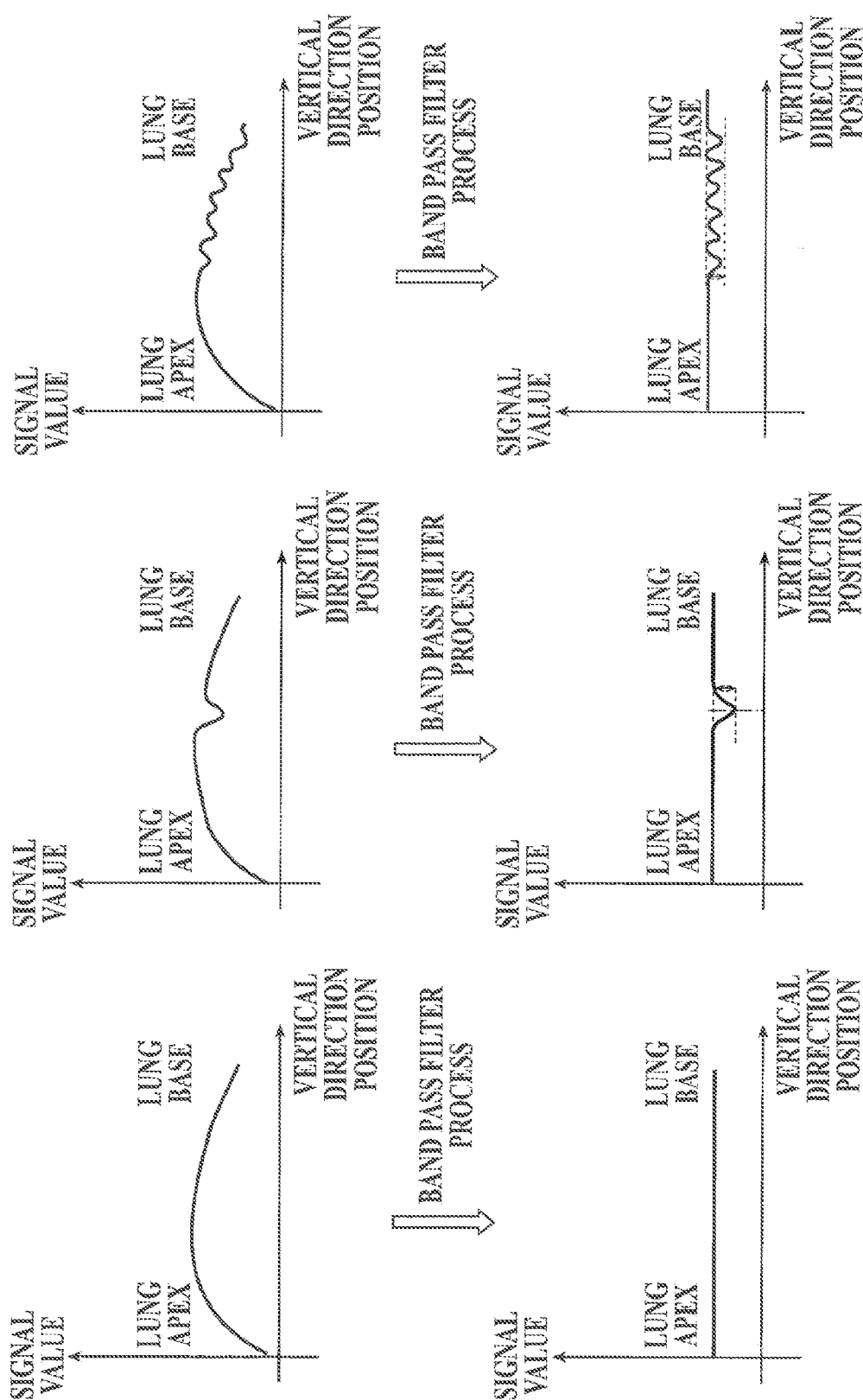

IMAGE PROCESSING APPARATUS AND COMPUTER-READABLE RECORDING MEDIUM

BACKGROUND OF THE INVENTION

Field of the Invention

The present invention relates to an image processing apparatus and a computer-readable recording medium.

Description of Related Art

When an X-ray image of a thoracic portion is captured, in addition to a lung field as a diagnostic target, structures such as ribs, clavicles, shoulder blades, and vertebrae which cover the lung fields also appear. These interfere with diagnosis of the lung field.

For example, Japanese Patent Application Laid-Open Publication No. 2012-297 describes extracting structures such as ribs, clavicles, etc. from each one of the plurality of frame images of thoracic dynamic images and reduces spatial signal change in the extracted structure.

For example, Japanese Patent Application Laid-Open Publication No. 2003-298939 describes, in order to reduce image components of bones appearing in the lung field dynamic images, capturing is performed using radiation from a plurality of different energy and calculating the obtained images. With this, the image is obtained reducing the image components of bone tissue.

US Patent Application Publication No. 2005/0100208 describes studying in advance a simple thoracic X-ray image (still image) and a teacher image emphasizing the bones in order to make a trained filter using a neutral network. Then, the simple thoracic X-ray image obtained with radiation capturing is input to the trained filter to obtain the image with the bones emphasized. Further, the image with the bones emphasized is subtracted from the simple thoracic X-ray image obtained by radiation capturing in order to obtain the image with the bones reduced.

US Patent Application Publication No. 2014/0079309 describes preventing misidentification of one rib by estimating the approximate position of the bone using a rib model (entire lung model, individual rib model) in a rib reducing process on a simple thoracic X-ray image (still image).

However, in dynamic images showing movement of a predetermined site or in a group of images in which a plurality of images captured by applying same energy, that is, irradiating an X-ray with the same tubular voltage on a same site of a same subject are aligned in a time series for comparison between the present image and the past image, when the predetermined structures such as the ribs and the clavicles are reduced, if the structure extraction is performed separately for each frame image or reduction of the spatial signal change due to structures is performed as described in Japanese Patent Application Laid-Open Publication No. 2012-297, the degree of reduction of the spatial signal change due to structures is different according to the frame image in a group of images in a time series.

For example, when the bone reduction is performed with the ribs and clavicles as the target of reduction in the thoracic dynamic images, one rib in a frame image may not be correctly extracted and not reduced whereas this rib may be successfully extracted and reduced in the frame image before and after the above frame image. If such group of frame images with the rib reduced is displayed as a movie or the difference is extracted by the frame difference process, the change in the density among the frames including the rib which could not be extracted becomes large. As a result, the reduced rib is actually rather emphasized.

According to the technique described in Japanese Patent Application Laid-Open Publication No. 2003-298939, the bones can be accurately extracted. However, a mechanism to switch and irradiate X-rays with different energy within a short time becomes necessary. As a result, the cost of the capturing apparatus increases.

The technique described in US Patent Application Publication No. 2005/0100208 is a technique used on a simple X-ray image. Therefore, this cannot solve the problem of the degree of reduction of the spatial signal change due to structures differing among the frame images in the dynamic images. In order to accurately apply the above technique to the reduction of bones in the dynamic images, trained filters need to be prepared for each image of each phase of breathing. Then, the breathing phase in each frame image of the dynamic images is determined and the trained filter for each phase needs to be applied. Such process is troublesome.

According to the technique described in US Patent Application Publication No. 2014/0079309, a rib model (entire lung model, individual rib mode) is used but the state of the ribs is different in each person. Further, other than bones (ribs/clavicles), tissues of blood vessels, tracheae, abnormalities, etc. appear in the lung region of the thoracic simple X-ray image, and the sizes and positions are different in each individual. Therefore, it is not possible to apply a uniform reference rib model to all ribs of all individuals. The positioning of the patient in the capturing depends on the operator and the patient and changes in each capturing. The image may also change depending on the capturing apparatus and the applied image process. Therefore, features of the ribs such as position, size, density gradient may often be outside the scope of the rib model. As a result, it becomes impossible to completely prevent misidentification of the ribs with the rib model.

BRIEF SUMMARY OF THE INVENTION

An object of the present invention, which has been conceived to solve the problem described above, is to provide a simple apparatus to accurately reduce spatial signal change due to predetermined structures in a group of X-ray images in which a plurality of images obtained by capturing the same site of the same subject a plurality of times are aligned in a time series.

According to one aspect of the present invention, there is provided an image processing apparatus including: a structure reducing unit which reduces spatial signal change by a predetermined structure in an X-ray image group in which a plurality of images obtained by capturing a same site of a same subject a plurality of times using an X-ray are aligned in a time series, wherein the structure reducing unit reduces the spatial signal change by the predetermined structure in each image of the X-ray image group using information of an image different from the image of the X-ray image group being processed.

According to another aspect of the present invention, there is provided a non-transitory computer-readable recording medium having a program stored thereon for controlling a computer used in an image processing apparatus which reduces spatial signal change by a predetermined structure in a X-ray image group in which a plurality of images obtained by capturing a same site of a same subject a plurality of times using an X-ray are aligned in a time series, wherein the program controls the computer to function as: a structure reducing unit which reduces the spatial signal change by the predetermined structure in each image of the X-ray image group using information of an image different from the image of the X-ray image group being processed.

BRIEF DESCRIPTION OF THE DRAWINGS

The present invention will become more fully understood from the detailed description given hereinbelow and the appended drawings, and thus are not intended to define the limits of the present invention, and wherein;

FIG. 9A is a diagram showing an example of a method to determine a frame with a weak bone reduction degree;

FIG. 9B is a diagram showing an example of a method to determine a frame with a weak bone reduction degree; and FIG. 9C is a diagram showing an example of a method to determine a frame with a weak bone reduction degree.

DETAILED DESCRIPTION OF PREFERRED EMBODIMENTS

First Embodiment

A first embodiment of the present invention is described in detail with reference to the drawings. The scope of the invention is not limited to the illustrated examples.
[Configuration of Dynamic Image Diagnostic Assistance System 100]

First, the configuration is described.

Figure 1:
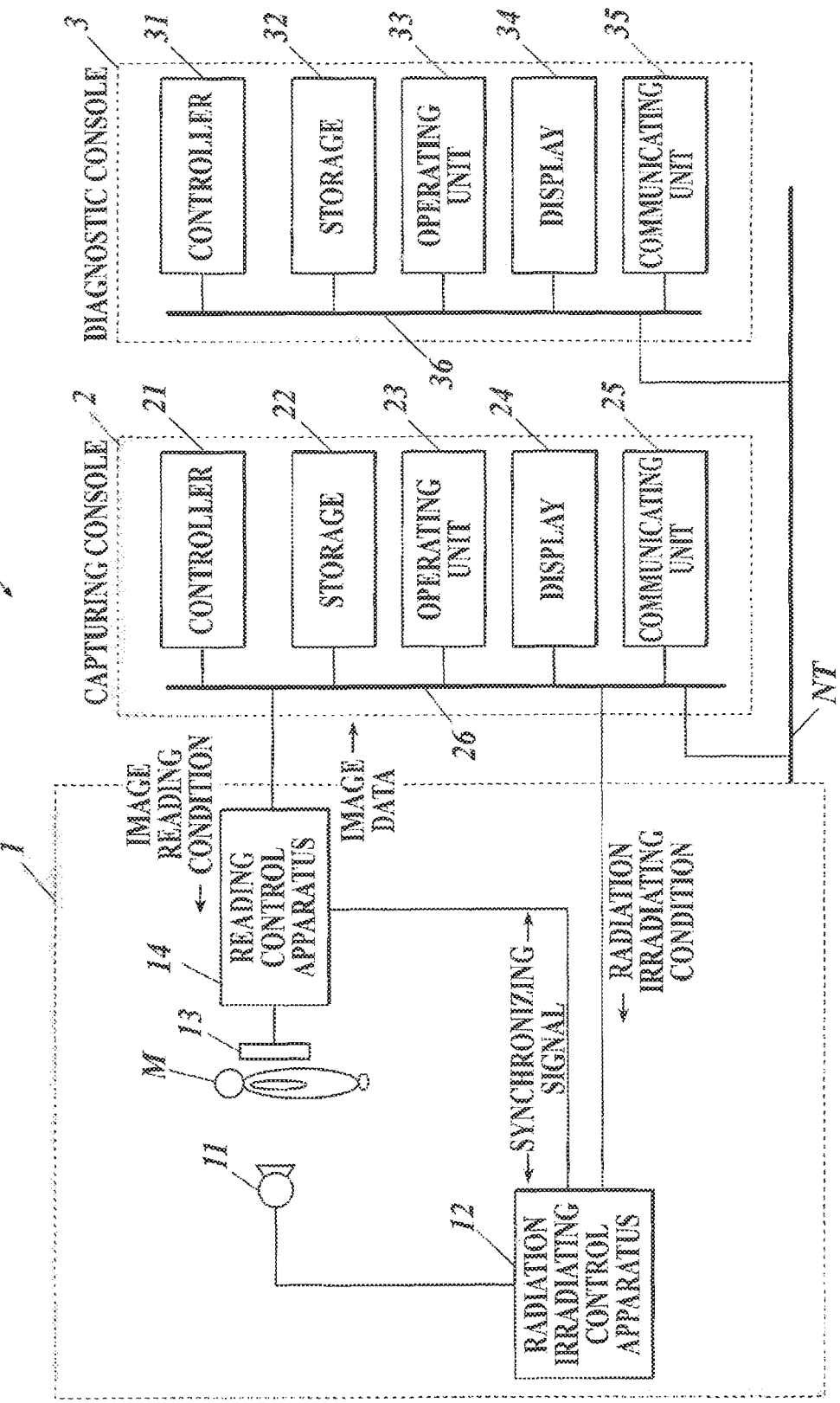
FIG. 1 is a diagram showing an entire configuration of a dynamic image diagnostic assistance system according to an embodiment of the present invention.

FIG. 1 shows an entire configuration of a dynamic image diagnostic assistance system 100 according to the present embodiment.

As shown in FIG. 1, the dynamic image diagnostic assistance system 100 includes a capturing apparatus 1, a capturing console 2, and a diagnostic console 3. The capturing apparatus 1 is connected to the capturing console 2 through a communication cable, etc. The capturing console 2 is connected to the diagnostic console 3 through a communication network NT such as a LAN (Local Area Network), etc. The apparatuses composing the dynamic image diagnostic assistance system 100 conform to DICOM (Digital Image and Communications in Medicine) standards, and the communication among the apparatuses is performed according to DICOM.
[Configuration of Capturing Apparatus 1]

The capturing apparatus 1 is an apparatus to capture periodic (cycle) movement of a thoracic portion such as change in the shape of the lungs inflating and deflating according to breathing, beating of the heart, etc. Dynamic capturing is performed by successively performing radiation (X-ray) capturing a plurality of times on a thoracic portion of a subject and obtaining a plurality of images aligned in a time series (that is, successive capturing). The series of images obtained by such successive capturing is called dynamic images. Each of the plurality of images composing the dynamic images is called a frame image.

As shown in FIG. 1, the capturing apparatus 1 includes a radiation source 11, a radiation irradiating control apparatus 12, a radiation detector 13, a reading control apparatus 14, and the like.

The radiation source 11 is positioned opposed to the radiation detector 13 with a subject M in between, and irradiates radiation (X-ray) to the subject M according to control by the radiation irradiating control apparatus 12.

The radiation irradiating control apparatus 12 is connected to the capturing console 2 and controls the radiation source 11 based on the radiation irradiating condition input on the capturing console 12 and performs radiation capturing. The radiation irradiating conditions input on the capturing console 2 include, for example, pulse rate, pulse width, and pulse interval in successive irradiation, capturing start and end timing, value of X-ray tubular current, value of X-ray tubular voltage, filter type, etc. The pulse rate is the number of times that radiation is irradiated for each second and matches with a later-described frame rate. The pulse width is the amount of time that radiation is irradiated each time the radiation is irradiated. The pulse interval is the amount of time from the start of one irradiation of radiation to the start of the next irradiation of radiation in successive capturing, and matches with a later-described frame interval.

The radiation detector 13 includes a semiconductor image sensor such as a FPD. The FPD includes, for example, a glass substrate. The FPD detects radiation which is irradiated from the radiation source 11 to a predetermined position on the substrate and which passes through at least the subject M according to the strength of the radiation. A plurality of pixels which converts the detected radiation to an electric signal and accumulates the electric signal is arranged in a matrix. Each pixel includes a switching unit such as a TFT (Thin Film Transistor).

The reading control apparatus 14 is connected to the capturing console 2. The reading control apparatus 14 controls the switching unit of each pixel in the radiation detector 13 based on an image reading condition input on the capturing console 2 to switch reading of the electric signal accumulated in each pixel. The reading control apparatus 14 reads the electric signal accumulated in the radiation detector 13 to obtain the image data. The image data is the frame image. Then, the reading control apparatus 14 outputs the obtained frame image to the capturing console 2. For example, the image reading condition includes a frame rate, a frame interval, a pixel size, an image size (matrix size), etc. The frame rate is the number of frame images obtained for each second and matches with the pulse rate. The frame interval is the time from the start of obtaining one frame image to the start of obtaining the next frame image in successive capturing, and matches with the pulse interval.

Here, the radiation irradiating control apparatus 12 and the reading control apparatus 14 are connected to each other, and exchanges synchronizing signals to tune the operation of radiation irradiating operation with the operation of reading the image.

[Configuration of Capturing Console 2]

The capturing console 2 outputs the radiation irradiating condition and the image reading condition to the capturing apparatus 1 and controls the radiation capturing and the reading of the radiation image by the capturing apparatus 1. The capturing console 2 displays the dynamic images obtained from the capturing apparatus 1 for confirmation of positioning by the capturing technician or to confirm whether the image is suitable for diagnosis.

As shown in FIG. 1, the capturing console 2 includes a controller 21, a storage 22, an operating unit 23, a display 24, a communicating unit 25 and all units are connected to each other through a bus 26.

The controller 21 includes a CPU (Central Processing Unit), a RAM (Random Access Memory), etc. In response to operation on the operating unit 23, the CPU of the controller 21 reads a system program and various processing programs stored in the storage 22 and deploys the programs in the RAM. The CPU executes various processes such as a later-described capturing control process according to the deployed program and centrally controls the operation of each unit in the capturing console 2 and the radiation irradiating and reading in the capturing apparatus 1.

The storage 22 includes a nonvolatile semiconductor memory, a hard disk, or the like. The storage 22 stores various programs executed by the controller 21, parameters necessary to execute the processes according to the program, or data such as result of the processes. For example, the storage 22 stores the capturing control process program to perform the capturing control process shown in FIG. 2. The storage 22 stores the radiation irradiating condition and the image reading condition corresponded with the examination target site. Various programs are stored as readable program codes, and the controller 21 executes operation according to the program code.

The operating unit 23 includes a keyboard including cursor keys, numeral input keys, various function keys and the like, and a pointing device such as a mouse. The operating unit 23 outputs to the controller 21 the instruction signal input according to key operation on the keyboard and mouse operation. The operating unit 23 may include a touch panel on the display screen of the display 24. In this case, the instruction signal input through the touch panel is output to the controller 21.

The display 24 includes a monitor such as a LCD (Liquid Crystal Display), a CRT (Cathode Ray Tube), etc., and displays input instructions from the operating unit 23, data, etc. according to instructions from display signals input from the controller 21.

The communicating unit 25 includes a LAN adaptor, a modem, a TA (Terminal Adapter), etc. and controls the transmitting and receiving of data between apparatuses connected to the communication network NT.

[Configuration of Diagnostic Console 3]

The diagnostic console 3 is an image processor which obtains the dynamic images from the capturing console 2, and displays the obtained dynamic images for diagnosis by a physician.

As shown in FIG. 1, the diagnostic console 3 includes a controller 31, a storage 32, an operating unit 33, a display 34, and a communicating unit 35, and the units are connected to each other through a bus 36.

The controller 31 includes a CPU, a RAM, etc. The CPU of the controller 31 deploys a system program stored in the storage 32 and reads various processing programs in the RAM in response to operation on the operating unit 33. The CPU performs various processes such as a later described bone reduction process according to the deployed programs and centrally controls the operation of each unit of the diagnostic console 3. The controller 31 performs the bone reduction and functions as a structure reduction unit, an extracting unit, a comparing unit, a reduction unit, a re-extracting unit, an acknowledging unit, a density profile creating unit, and a density profile correcting unit.

The storage 32 includes a nonvolatile semiconductor memory, a hard disk, etc. The storage 32 stores various programs such as a program to execute the bone reduction process in the controller 31, parameters necessary to execute the process according to the program, or data such as the processing result. The various programs are stored in a form of a readable program code, and the controller 31 performs operation according to the program code.

The operating unit 33 includes a keyboard including cursor keys, numeric input keys, various function keys, and the like, and a pointing device such as a mouse. The operating unit 33 outputs the instruction signal input by key operation on the keyboard or mouse operation to the controller 31. The operating unit 33 may include a touch panel on the display screen of the display 34, and the instruction signal input through the touch panel is output to the controller 31.

The display 34 includes a monitor such as a LCD, CRT, and the like, and displays input instructions from the operating unit 33, data and the like according to instructions from display signals input from the controller 31.

The communicating unit 35 includes a LAN adaptor, a modem, a TA, etc. and controls the transmitting and the receiving of data between apparatuses connected to the communication network NT.

[Operation of Dynamic Image Diagnostic Assistance System 100]

Next, the operation in the dynamic image diagnostic assistance system 100 is described.

(Operation of Capturing Apparatus 1, Capturing Console 2)

First, the capturing operation by the capturing apparatus 1 and the capturing console 2 is described.

Figure 2:
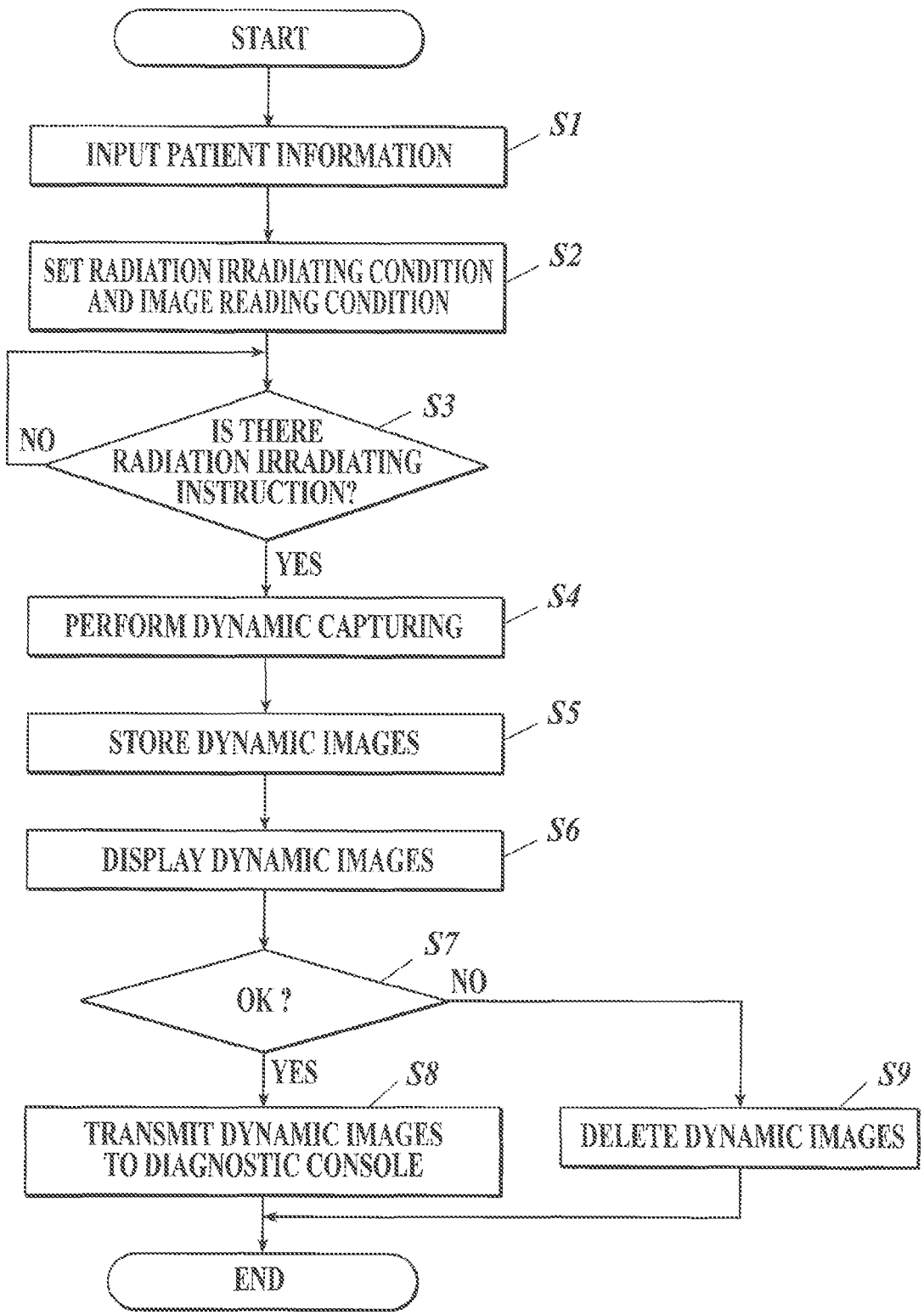
FIG. 2 is a flowchart showing a capturing control process performed by a controller of a capturing console shown in FIG. 1.

FIG. 2 shows a capturing control process executed in the controller 21 of the capturing console 2. The controller 21 executes the capturing control process in coordination with a capturing control process program stored in the storage 22.

First, the capturing technician operates the operating unit 23 of the capturing console 2 and inputs the patient information (name, height, weight, age, sex, etc. of the patient) of the capturing target (subject M) (step S1).

Next, the radiation irradiating condition is read from the storage 22 and set in the radiation irradiating control apparatus 12. The image reading condition is read from the storage 22 and set in the reading control apparatus 14 (step S2).

Next, the apparatus stands by for the instruction to irradiate radiation according to operation on the operating unit 23 (step S3). At this time, the capturing technician positions the patient. Specifically, the subject M is positioned so that the front (or the back or the side) of the thoracic portion of the subject M faces the radiation source 11. When the positioning ends, the capturing technician operates the operating unit 23 to instruct irradiation of radiation.

When the radiation irradiating instruction is input on the operating unit 23 (step S3; YES), the capturing start instruction is output to the radiation irradiating control apparatus 12 and the reading control apparatus 14 and the dynamic capturing starts (step S4). That is, the radiation source 1 irradiates radiation at a pulse interval set in the radiation irradiating control apparatus 12 and the frame image is obtained by the radiation detector 13. When a predetermined amount of time passes from the start of the dynamic capturing, the controller 21 outputs an instruction to end capturing to the radiation irradiating control apparatus 12 and the reading control apparatus 14 to stop capturing operation. According to the dynamic capturing, X-ray with substantially the same energy, that is, substantially the same tubular voltage is irradiated a plurality of times to obtain the plurality of frame images.

The frame images obtained by the capturing are sequentially input in the capturing console 2. The images are corresponded with a number showing the order of capturing and stored in the storage 22 (step S5). The images are also displayed on the display 24 (step S6). The capturing technician confirms the positioning with the displayed dynamic images, and determines whether the image suitable for diagnosis is obtained by the capturing (capturing OK) or capturing needs to be performed again (capturing NG). The operating unit 23 is operated to input the result of determination.

When the result showing capturing OK is input by a predetermined operation on the operating unit 23 (step S7; YES), the information described below is added to each one of the string of frame image obtained by dynamic capturing (for example, written in the header of the image data in a DICOM format). The information includes an identification ID to identify the dynamic images, patient information, examination target site, radiation irradiating condition, image reading condition, number showing capturing order and the like. With the above information added, the frame images are transmitted to the diagnostic console 3 through the communicating unit 25 (step S8). Then, the process ends. When the result showing capturing NG is input by a predetermined operation on the operating unit 23 (step S7; NO), the string of frame images stored in the storage 22 is deleted (step S9), and the process ends.

(Operation of Diagnostic Console 3)

Next, the operation in the diagnostic console 3 is described.

In the diagnostic console 3, when a string of frame images composing the dynamic images is received from the capturing console 2 through the communicating unit 35, the bone reduction process is performed.

Figure 3:
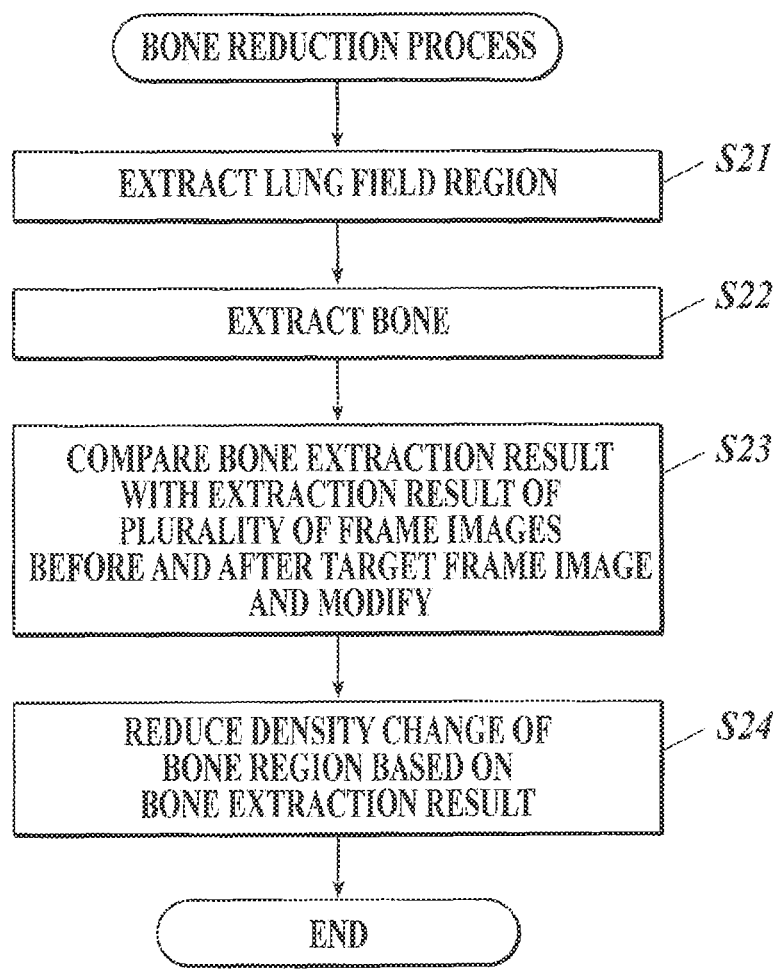
FIG. 3 is a flowchart showing a bone reduction process performed by a controller of a diagnostic console shown in FIG. 1.

FIG. 3 shows a flowchart of the bone reduction process. The bone reduction process is executed by the controller 31 in coordination with the program stored in the storage 32.

According to the bone reduction process, first, a lung field region is extracted for each frame image (step S21), and then a bone is extracted from the lung field region (step S22).

Any method can be used to extract the lung field region in step S21. For example, the threshold can be obtained by analyzing the histogram of the signal value (density value) in each pixel of the frame image and the region with the signals larger than the threshold is first extracted as the lung field region candidate (primary extraction). Next, edge detection is performed in the boundary of the extracted lung field region candidate, and the point where the edge is the largest in the small region near the boundary is extracted along the boundary. With this, the boundary of the lung field region can be extracted.

The technique described in US Patent Application Publication No. 2014/0079309 can be used in the bone extraction process in step S22.

First, (1) a bone candidate region is extracted from the frame image. The extraction of the bone candidate region can be performed by, for example, template matching with a preset rib template or clavicle template, edge detection, or applying a curve fitting function after edge detection.

Next, (2) it is carefully examined whether the region is the bone candidate region or the bone region, and the region is labeled showing whether the region is the bone region or not. For example, referring to previous knowledge regarding the structure of the bones such as the rib and the clavicle, it is carefully determined whether the extracted bone candidate region is the bone region based on features such as position, shape, size, density gradient, direction, etc. The overly extracted portion is discriminated and removed from the bone candidate region. After flattening the boundary of the bone candidate region by a morphological process, the pixels for each region corresponding to each bone of the ribs or the clavicles are grouped as the bone region and labeled. For example, the regions are labeled by setting a predetermined value (here, 1) in the pixels of the bone region and 0 in the pixels of the non-bone region. Further, the region growth method can be used to extend the bone region corresponding to each bone of the ribs or the clavicles, or the separated small bone region can be combined. Here, the process to automatically extract the bone region by image processing is described as the bone extraction process. Alternatively, the user can check each frame image displayed on the display 34 of the diagnostic console 3 and manually input the bone region with the operating unit 33. Alternatively, first, the bone candidate region in each frame image can be automatically extracted by image processing, and then the user can check the bone candidate region in each frame image displayed on the display 34 of the diagnostic console 3. Then, the user can manually correct the bone candidate region on the operating unit 33 and determine the bone region in each frame image.

Here, the result (bone extraction result) labeled in each frame image can be checked using a typical bone model of a typical patient and the bone portion which is erroneously extracted in each frame image can be specified. The erroneously extracted portion which is specified can be processed by the above (1) bone candidate region extraction and (2) labeling again. Even if the results are not checked using the typical bone model, for example, as for the ribs, the space between the ribs in the vertical direction is a certain pattern, and the space between the ribs can be used to specify erroneously extracted rib portions. For example, the coordinates of the center position of the bone region in the vertical direction corresponding to each rib is extracted in the horizontal position (for example, center in the horizontal direction) where one lung is in the frame images and the space between the center positions of the bone region corresponding to the ribs is calculated. When the space is larger than a predetermined threshold or a certain space is significantly larger than other spaces, this portion is considered to be the erroneous extraction of the ribs, and the bone region candidate extraction and the bone labeling can be performed again. Repeating the bone candidate region extraction and the bone labeling in the bone extraction process can enhance the accuracy of bone extraction in each frame image.

Here, when the bone extraction process is applied to each frame image, contrast emphasis such as gradation processing and spatial filtering can be performed on the frame image data collected in the capturing as pervious processes. Alternatively, a frame difference image between the present frame image and the adjacent previous frame image can be applied to the bone extraction on each frame image as additional information. In dynamic images showing breathing, an image in which the edge of the bone is emphasized by the movement of the bone can be obtained by the frame difference from the adjacent previous frame image. Therefore, for example, by extracting the portion of the frame difference image with a predetermined threshold or more, the bone region can be roughly extracted. A detailed bone position detection by pattern recognition can be performed based on the roughly extracted bone region so as to enhance the accuracy of extracting the bones.

When the bone extraction of each frame image ends, the bone extraction result is checked and modified for each frame image using a plurality of frame images before and after the present image (step S23). According to the following description, the frame images before and after or the plurality of frame images before and after are a plurality of frame images before and after and successive to the target (processed) frame image (target frame image) (capturing order is before and after and successive to the target frame image).

For example, the bone extraction result (labeling) are compared among corresponding pixels for each pixel of a certain target frame image. The compared frame images include m-frame images (m is a positive integer) successive before the target frame image (capturing order is before), n-frame images (n is a positive integer) successive after the target frame image (capturing order is after), and the target frame image, that is m+n+1 frame images. When it is determined that the bone extraction result in a predetermined number or more (for example, more than half) images is the bone region, the pixel of the target frame image is considered to be the bone region regardless of the bone extracting result of the target frame image. If the bone extraction result of the pixel of the target frame image is the non-bone region, the labeling is modified to the bone region.

Similarly, if the pixel is determined to be the non-bone region in a predetermined number or more images among the m+n+1 frame images, the pixel of the target frame image is considered to be the non-bone region. Then, if the bone extraction result of the pixel of the target frame image is the bone region, the labeling is modified to the non-bone region.

Figure 4:
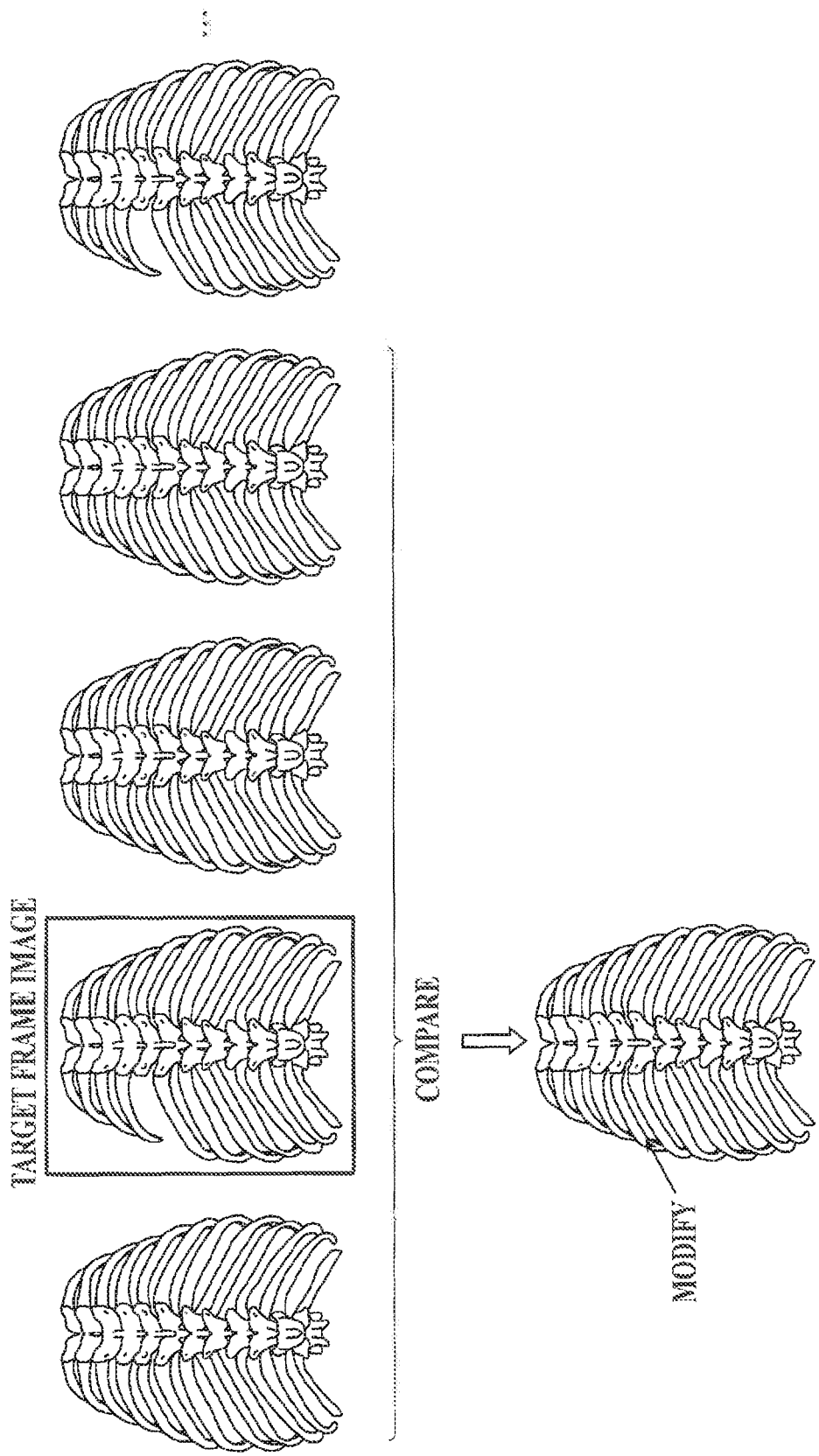
FIG. 4 is a diagram schematically showing the process of step S23 shown in FIG. 3.

FIG. 4 schematically shows the process in step S23, FIG. 4 shows an example in which m=1 and n=2. As shown in FIG. 4, in the target frame image, the bone region corresponding to one rib is not extracted due to error in extraction. However, by comparing the target frame image with the bone extraction region of one frame image before and the two frame images following the target frame image and correcting the target frame image, the bone which is not extracted due to error can be extracted. As described above, according to the process shown in step S23, it is possible to reduce the result of bone extraction being different among adjacent frame images. Moreover, it is determined whether the region is the bone region or not based on the extraction result of a plurality of frame images. Therefore, the accuracy of bone extraction is enhanced compared to extracting the bone using only each one of the frame images.

Preferably, in order to enhance accuracy of extraction m+n+1>3.

Figure 5:
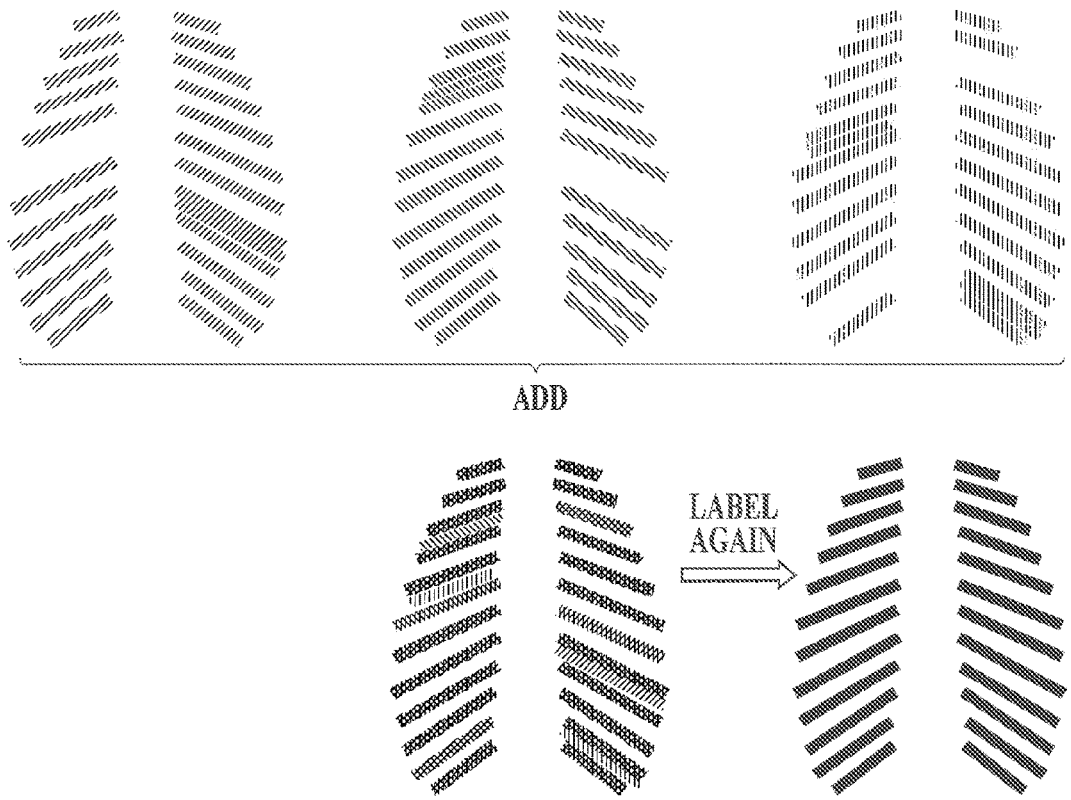
FIG. 5 is a diagram schematically showing an example of a specific checking and modifying method in step S23 shown in FIG. 3.

The method to check and modify the bone extraction result using a plurality of frame images may be the following as shown in FIG. 5. The bone extraction results labeling each pixel of the images to be checked (m+n+1 frame images) are added for each pixel in the m+n+1 frame images. Only the pixels with the added value resulting in a predetermined threshold or more are determined to be the bone region and labeled again. FIG. 5 shows an example in which m=n=1.

Figure 6:
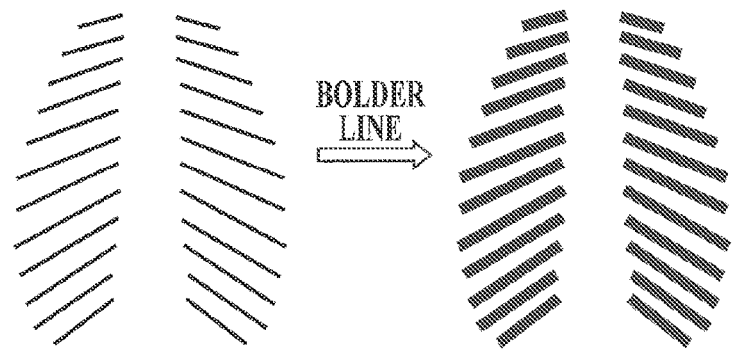
FIG. 6 is a diagram schematically showing an extracted bone region with bold lines.

When the dynamic images are captured while breathing, if the extraction results of the bone regions labeled in the m+n+1 frame images are added, and the pixels in which the added results are a predetermined threshold or more are relabeled as the bone region, the width of the bone region corresponding to each one of the relabeled rib or clavicle may be smaller (thinner) than the width of the bone region originally extracted in each image due to the bone moving by breathing. As shown in FIG. 6, a line thickening process can be applied to the bone region corresponding to each bone of the ribs and clavicles by morphology, etc. With this, the error of extraction as a region in the extracted bone region can be made smaller.

The following method can be applied to check and modify the bone extraction result.

Figure 7:
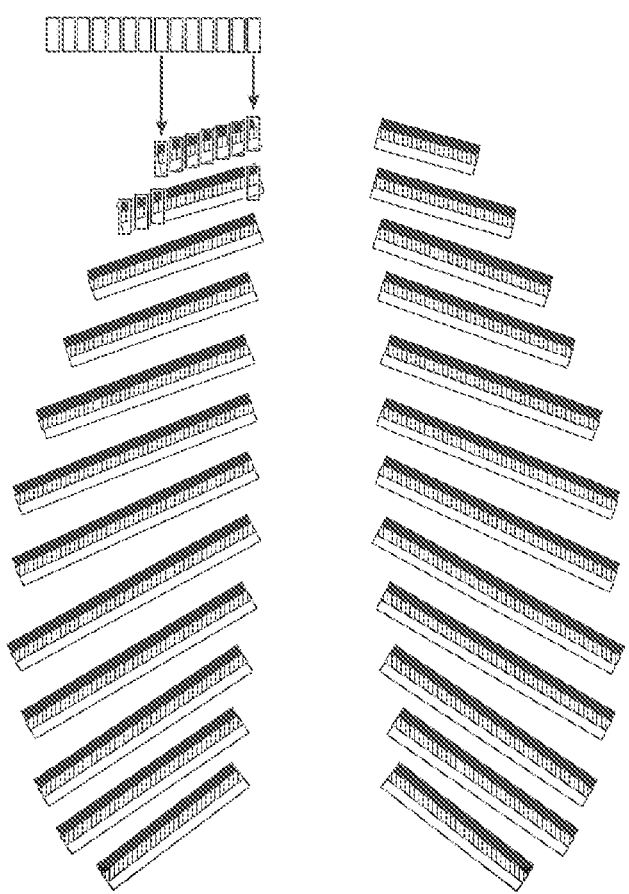
FIG. 7 is a diagram showing an example of another method to check and modify the bone extracting result.

As shown in FIG. 7, first, the line thinning process by morphology is applied or the central line in the vertical direction is obtained for the bone region corresponding to each bone of the ribs and clavicles extracted using only the frame images. With this, the extracted bone region corresponding to each bone of the ribs and clavicles is expressed with a line having a width with a predetermined number of pixels (for example, one pixel) in the vertical direction of the image. Next, after labeling the pixel on the line with 1 and labeling the pixels other than the above with 0, the image adding m+n+1 frame images is made for each pixel. In FIG. 7, the setting is m=1, n=1, and FIG. 7 shows a schematic result adding the labeled values of three frame images composed of a target frame image and adjacent frame images (the labeling in the frame images is shown with 3 different patterns, black, diagonal lines, and white). As shown in FIG. 7, in the created image, for each column, small blocks composed of 1 pixel×k pixels are scanned in the vertical direction (in a direction from top to bottom). The small blocks in which the total value in each block is a predetermined threshold or more are relabeled as the bone region. Preferably, k pixels showing the size of the small block in the vertical direction is determined based on the movement amount of the bones by breathing. According to the above method, the shift of the bone among frames due to the movement of the bone with breathing can be considered when the bone extraction result is checked among the plurality of frame images and the bone region is extracted. If necessary, processes such as morphology can be applied on the relabeled bone region and the region can be enlarged by thickening the line.

Alternatively, the following process is possible. The information ($\alpha_1$ to $\alpha_{m+n+1}$) of the bone extraction result for each pixel or each small block in each frame image can be labeled with bone region=1, non-bone region=0. Weighting coefficients $\beta$ ($\beta_1$ to $\beta_{m+n+1}$) can be assigned to each frame image composing the m+n+1 frame images so that the multiplied value becomes 1. The inner product S (following formula 1) of $\alpha_1$ to $\alpha_{m+n+1}$ and $\beta_1$ to $\beta_{m+n+1}$ can be defined as the index value showing whether there is a bone in the region of the target frame image. Then, only when the value S exceeds the predetermined threshold, the pixel or the small block of the target frame image is determined to be the bone region, and the bone extraction result of the region in the target frame image can be exchanged with the label of bone region=1.

$$S=\alpha_1\times\beta_1+\alpha_2\times\beta_2+\ldots+\alpha_{m+n+1}\times\beta_{m+n+1} \quad \text{(formula 1)}$$

Here, if there is a higher possibility of no extraction occurring more than the excess extraction in the bone region in the bone extraction of each frame image, the threshold is set to a value close to 0 so that the determining result based on the index value S is more likely to be determined as the bone region. If there is a higher possibility of excess extraction more than no extraction of the bone region, the threshold in the process is set to a value close to 1 so that the determining result based on the index value S is more likely to be determined as the non-bone region.

The number of frame images before and after the target frame image used to check the bone extraction result and the weighting coefficient β of each frame can be changed. For example, in the dynamic images captured during breathing, the edge of the diaphragm can be extracted and followed to understand the breathing state, that is, the phase in the breathing cycle (breathing phase) in each frame image. In the frame images of the phases where the movement amount of the diaphragm is small among the adjacent frame images such as inhale to exhale or exhale to inhale, the number of frame images before and after the target image which are used for checking is increased or the weighting coefficient β is an almost uniform value and a coefficient value close to the movement average is set. In the frame images of phases where the movement amount of the diaphragm is large, such as the phase of the center of the inhaling or the exhaling, the number of frame images before and after the target image which are used for checking is reduced or a weighting coefficient β with a large value is applied to the target frame image and a smaller value is set for farther frames.

As described above, as for the frame images of phases in which the movement amount of the diaphragm is small, more frame images before and after the target image are to influence the target image. As for the frame images of phases in which the movement amount of the diaphragm is large, only the frame images before and after the target which are close in terms of time influence the target image. With this, it is possible to prevent bad influences caused by movement of the bone among frames due to breathing when the bone extraction result is checked using the frame images before and after the target frame image.
Consequently, the bone extraction accuracy can be enhanced.

The phase of breathing in each frame image can be identified by the output value of a sensor such as a breath flow sensor (not shown) which is provided on the capturing apparatus.

When information (dose information) of the irradiating amount of the X-ray irradiated in capturing is added to the entire set of dynamic images or each frame image of the dynamic images, the number of frame images before and after the target image which are used for checking the bone extraction result and the weighting coefficient β of the frame images can be changed according to the added dose information. For example, as the amount of X-ray irradiation on the frame images in capturing becomes smaller, the noise increases in the image and errors in extraction of the bone tend to occur. Therefore, the number of frame images before and after the target image used for checking may be increased as the value of the added dose information becomes smaller. Alternatively, the weighting coefficient β can be an almost uniform value, and a coefficient value which becomes closer to the movement average can be set. With this, the bone extraction result can be corrected based on the bone extraction results of more frame images before and after the target frame image even when the X-ray irradiating amount is small. Consequently, the accuracy of bone extraction can be enhanced.

When the bone extraction result is checked and modified for each frame image using the plurality of frame images before and after the target image, preferably, the checking and modifying is performed after deforming and positioning the lung field region (rib cage) in the m frames before and n frames after the target frame image so as to match with the lung field region (rib cage) of the target frame image. The method of matching the position can be performed using the local matching process and the warping process. With this, the influence of breathing can be suppressed to a small influence, and the bone region of the target frame can be extracted more accurately based on the bone extraction result of the plurality of frames before and after the target frame.

According to the description above, the bone extraction result is corrected as a result of checking in the region determined to have a different result from the plurality of frame images before and after the target image. Alternatively, the process in step S22 can be done again based on the checking result. For example, based on the relabeled bone region, the parameter is changed and the extraction of the bone candidate region is performed again, the obtained bone candidate region is carefully examined to determine whether the region is the bone region or not. The region is labeled as the bone region or the non-bone region and the checking of the bone extraction result is performed. For example, when the bone candidate extraction is performed again, template matching can be performed using the rib template or clavicle template made based on the relabeled bone region in the above checking of the bone extraction result. Alternatively, edge extraction can be performed along the relabeled bone region or the nearby region. Then, based on the bone extraction result performed again, the bone reduction which follows is performed. With this, the correction of the bone extraction result is not applied as is, but the bone extraction result is the region actually extracted from the target frame image based on the correction. With this, the extraction can be performed based on the information of the actual target frame image. For example, instead of the dynamic images, when the bone region is extracted and reduced in a group of images composed of the present X-ray image and the past X-ray images for the same site of the same subject, the bone extraction result of the target frame image may be different from the bone extraction result of the other frame images. Therefore, it is preferable to perform the extraction process of the bone candidate region again based on the relabeled correction result.

According to the above description, the bone extraction result is checked after the bone extraction. Alternatively, after the bone candidate region is extracted, the result of the bone candidate region extraction process of the plurality of frame images before and after the target image can be checked, and as a result of checking, if it is determined that the extraction result of the bone candidate region is different from the plurality of frame images before and after the target image, the bone candidate region extraction can be performed again. Since careful examination of whether the region is the bone region based on the features of the bone structure is not performed in the bone candidate extraction, there are many regions erroneously extracted by excess extraction of the bone regions. Therefore, if the extraction result of the bone candidate region of the target frame image is compared with the result of the bone candidate region of the plurality of frames before and after the target frame image, the process may respond to the bone regions which are excessively extracted, and may rather increase erroneously extracted regions. Therefore, as described above, preferably, the comparison between the target frame image and the plurality of frame images before and after the target frame image is performed using the bone extraction result after labeling the bone regions and carefully examining whether the region is the bone region or not.

When the checking and the modifying of the bone extraction result in step S23 ends, the density subtraction of the bone region is performed based on the bone extraction result (step S24). Specifically, the bone region is specified based on the bone extraction result for each frame image, and a density profile of the cross-section of the bone is made for the specified bone region corresponding to each bone of the ribs and the clavicles. Then, the low-pass filter is applied to the made density profile to remove spatial high frequency component such as noise. The value of the density profile with the noise, etc. removed is subtracted from the original frame image. With this, the image with the change in density of the bone (spatial signal change) reduced can be obtained.

As described above, by checking and correcting the bone extraction result of each frame image using one to a plurality of different frame images instead of using only the target frame image itself, the process of reducing the signal component of the bone (spatial signal change due to the bone such as the ribs or clavicles) can be performed based on the bone region after checking and modifying. Therefore, the bone region can be reduced accurately. As a result, it is possible to prevent the problem of only one rib or clavicle not being reduced and rather being emphasized in a certain frame image in the dynamic images.

Figure 8:
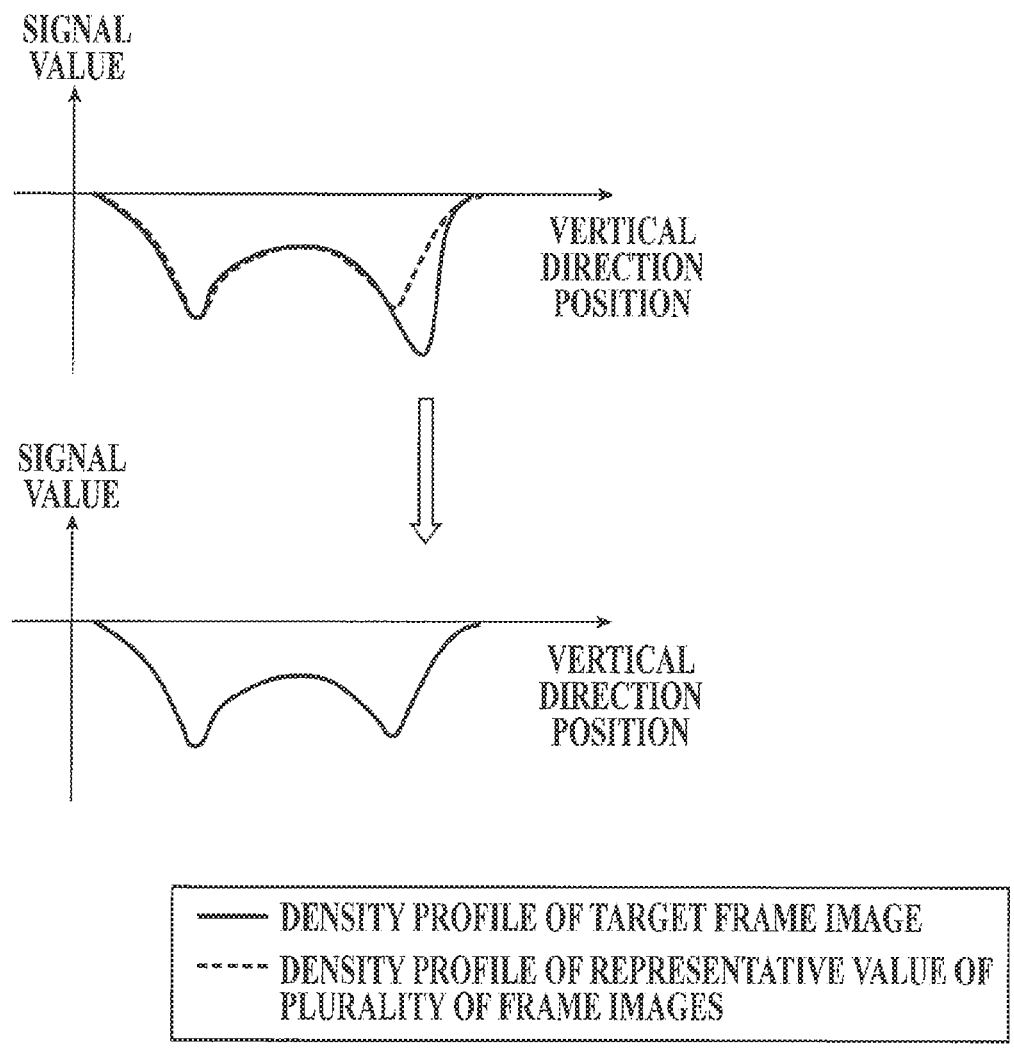
FIG. 8 is a diagram showing an example of checking and modifying a density profile.

Here, the density profile of the cross-section of the bone corresponding to each bone of the rib and the clavicle plots the change of the density in the cross-section of the bone with the horizontal axis showing the position in the vertical direction of the frame image and the vertical axis showing the density value (signal value) as shown in FIG. 8.

Preferably, before the density profile of the cross-section of the bone is subtracted from the frame image, the density profile is compared with the density profile created for the plurality of frame images before and after the target frame image, and the subtracted value is corrected to substantially match with the plurality of frame images before and after the target image.

For example, for each pixel of the target frame image, the value of the density profile in the cross-section of the bone is compared with the representative value (for example, central value) obtained from the density profile of the corresponding pixel in the plurality of frame images before and after the target frame image or the value of the density profile in the adjacent frame image (frame image directly before or after the target frame image). When there is a difference equal to or larger than the predetermined threshold, the density profile of the target frame image is corrected by, for example, replacing the value with the compared value (representative value). Alternatively, as shown in FIG. 8, the degree of match of the waveform is evaluated in the same positions by obtaining the correlation (for example, cross-correlation function) between the waveform of the density profile of the cross-section of the bone in the position in the horizontal direction of the target frame image and the waveform of the same position obtained from the representative value of the density profile in the plurality of frame images before and after the target frame image (for example, the waveform formed from the central value of each density profile) or the waveform of the density profile of the adjacent frame image in the same position (frame image directly before or after the target frame image). When the degree of match (correlation value) is less than the predetermined threshold, the entire density profile of each position in the horizontal direction of the target frame image can be corrected by substituting with the compared waveform.

With this, in the bone density subtraction process, since the value of the density profile to be subtracted from the original frame image substantially matches with the plurality of frame images before and after the target frame image, it is possible to prevent the image after bone reduction becoming significantly different from the plurality of frame images before and after the target image. For example, it is possible to erase the influence of variation for each frame image in the bone reduction process when the difference is calculated for each corresponding pixel or corresponding region among the different frame images such as the adjacent frame images, and it is possible to better extract only the change in the lung field due to breathing.

Alternatively, the density profile can be adjusted by multiplying the same constant to each value of the density profile in the cross-section of the bone in a certain position of the target frame image so that the integrated value of the waveform of the density profile in the cross-section of the bone in the certain position in the horizontal direction in the target frame image matches with the integrated value of the waveform obtained from the representative value of the density profile of the plurality of frame images before and after the target image in the same position or the integrated value of the waveform of the density profile of the adjacent frame images (frame image directly before or after the frame image) in the same position. The integrated value here is not limited to the waveform of the density profile in the cross-section of the bone in the certain position and can also be the integrated value of the total density profile of the bone region for one bone of the rib, the integrated value of the total density profile of the bone region dividing one lung region into three regions in the vertical direction, or the integrated value of the total density profile of one lung region or total lung region. The density profile value can be adjusted by multiplying the same constant number to the value for the total density profile to the certain region of the target frame image so that the integrated value of the total density profile matches in the corresponding region.

With this, the integrated value of the density profile subtracted from the original frame image in the bone density subtraction process substantially matches with the plurality of frame images before and after the target image. Consequently, it is possible to prevent the image after the bone reduction process being significantly different from the plurality of frames before and after the target frame image. For example, when the difference is calculated for corresponding pixels or corresponding regions between different frames such as adjacent frames, the influence on the bone reduction process due to variation in each frame can be eliminated and it is possible to better extract only the change in the lung field due to the breathing.

After applying the bone reduction process on each frame image of the group of images, each frame image is compared with the plurality of frame images before and after the target frame image and the image after the bone reduction process. The frame image with the weak degree of bone reduction is extracted. When the frame image with the weak degree of bone reduction is extracted, the bone reduction process may be performed again in only the extracted frame image or the entire image group. For example, the density profile in the lung field in the vertical direction is calculated for the image after bone reduction in the horizontal position in the lung field such as the center position of the width of one lung or a position ¼ from the outer side. If the change of the density profile is large compared to the plurality of frame images before and after the target frame image, it is determined that the degree of the bone reduction is weak and the bone reduction process is repeated.

The following method is used as the determining method of the frame with the weak degree of bone reduction. For example, when the target is the ribs, as shown in FIG. 9A to FIG. 9C, a band pass filter is applied in the spatial direction on the density profile of each frame image. The density inclination of the low frequency by muscles and fat and other high frequency noise components are removed to extract the density change components on the substantial rib cycle in the vertical direction. The density change after filtering is compared with the plurality of frame images before and after the target frame image and the frame image with a significantly large density change amount (shown with an arrow in FIG. 9B and FIG. 9C) compared to the other frame images (for example, the density change amount is larger than the average of the plurality of frame images before and after the target frame image in a value equal to or larger than the predetermined threshold) is determined to be the frame image with the weak reduction degree (frame image with a low degree of bone reduction compared to other frame images). Alternatively, the density change after filtering can be compared among a plurality of images in substantially the same position in the vertical direction, and with this, the bone region of a predetermined position can be specified to determine whether the degree of bone reduction is weak.

A certain frame image after the bone reduction process may suddenly have a weak degree of bone reduction and the density change among frame images may become large. Therefore, the difference image between adjacent frames can be generated for the image after the bone reduction process, and the region in which the difference value exceeds the predetermined threshold can be extracted in the adjacent frame difference images for the plurality of frame images before and after the target frame image to determine the region with the weak degree of bone reduction.

When the frame image with the weak degree of bone reduction is extracted and the region with the weak degree of bone reduction is specified in the frame image, the bone extraction process is performed again in such region. Alternatively, the density profile of the cross-section of the bone subtracted in the bone density subtraction process may not be correctly generated. Therefore, the bone extraction result is not changed. For example, in the bone density subtraction process, the profile is made again with the parameters in the low-pass filter changed when the density profile of the bone cross-section is calculated, or only the bone density subtraction process is performed again by using the density profile used in the bone density subtraction of the region in the nearby frame images before and after the target frame image. As described above, the images of the plurality of frame images before and after the target frame image and the image after the bone reduction process are compared for each frame image. The bone reduction process is performed again on the frame image with the weak degree of bone reduction compared to the plurality of frame images before and after the target frame image. Since the bone reduction process is performed again, the bone region can be accurately reduced to match the plurality of frames before and after the target frame image compared to the bone reduction process simply using a uniform typical bone model separately on each frame image.

When the images after the bone reduction process are checked for each frame image using the plurality of frame images before and after the target frame image, preferably, the images are checked after deforming or matching the position so that the lung field region (rib cage) of all of the plurality of frame images to be checked match with each other. With this, the influence of breathing can be suppressed to a small influence. Consequently, the frame image with the weak degree of bone reduction can be extracted accurately based on the image after the bone reduction process of a plurality of frame images before and after the target frame image.

Thoracic dynamic images with the bone reduced by the bone reduction process are displayed as a moving image on the display 34 by the controller 31. Alternatively, the frame difference process is performed among the adjacent frame images, and the obtained frame difference image is displayed on the display 34. Preferably, before the frame difference process, deforming and position matching is performed among the images with which the difference is obtained so that the lung field regions (rib cages) or the lung blood vessels match. The direction of movement is different in the lung blood vessel, ribs, and clavicles in breathing. The shadows of the ribs and the clavicles in the image become obstacles in matching the position of the lung blood vessels. According to the present method, the bone region such as the ribs and the clavicles in the image group in which a plurality of images are aligned in a time series are accurately decreased. Therefore, the deforming and the positioning to match the lung blood vessel performed in the frame images of the group of images can be accurately performed. The bone reduction process according to the present method is applied to both the past dynamic images and the present dynamic images. Pairs of corresponding frame images such as the order is the same or the phase is almost the same are sequentially extracted from both dynamic images. The two dynamic images including the extracted frame images can be displayed aligned as is or the frame difference process can be performed on the adjacent frame images of the dynamic images, and the obtained dynamic images can be displayed aligned. Since the two dynamic images with the bone region accurately reduced are displayed aligned, the dynamic images extracting only the change in the lung field due to breathing can be compared, and the difference in the change of breathing between the dynamic images can be detected accurately.

As described above, according to the bone reduction process of the present embodiment, the results of each frame image is checked using not only the target frame image itself but also one to a plurality of different frame images, and using the above frame images, the bone extraction result, the density profile of the bone cross-section subtracting the frame image and the image after the bone reduction process are checked. According to the above check results, processes such as performing the bone extraction process again with the bone extraction result corrected or the parameter changed, creating the density profile of the bone cross-section subtracted from the frame image again, performing the bone reduction process again are executed to more accurately reduce the bone region. As a result, in the group of images in which a plurality of images are aligned in a time series, it is possible to prevent one bone of the ribs or the clavicles not being reduced and rather being emphasized in a certain frame image.

According to the bone reduction process in the present embodiment, the bone region is reduced accurately and the group of images after the bone reduction is displayed or analyzed. With this, it is possible to better extract only the change in the lung field by breathing.

As described in US Patent Application Publication No. 2005/0100208, when the image with the bone emphasized through the trained filter is obtained for each frame image and this is subtracted from the original image to obtain the bone reduction image, as described above, not only the frame image itself but also one to a plurality of different frame images can be used to check the frame image after the bone reduction process. The frame image with the weak degree of bone reduction is extracted, and the bone reduction process is performed again using a different trained filter on only the extracted frame image or the entire group of images in the dynamic images. With this, the image after the bone reduction process being significantly different from the plurality of frames before and after the target frame image can be prevented. The influence of variation in each frame image in the bone reduction process can be eliminated when the difference value between the corresponding pixels or the corresponding regions is calculated among different frames such as adjacent frames. With this, it is possible to better extract only the change in the lung field due to breathing.

According to the above-described embodiment, a preferable example to accurately reduce the spatial signal change due to the bone is to always check the bone extraction result for each frame image using not only the target frame image itself but also one to a plurality of different frame images. Alternatively, when only either the checking of the density profile of the bone cross-section subtracted from the frame image or the checking of the image after the bone reduction process is performed, the reduction accuracy of the spatial signal change by the bone can be enhanced.

Second Embodiment

The second embodiment of the present invention is described below.

The configuration of the second embodiment is similar to the configuration described in the first embodiment and the description is incorporated herein. According to the second embodiment, the bone extraction process in step S22 shown in FIG. 3 is different from the first embodiment, and the bone extraction process in the second embodiment is described. Moreover, according to the second embodiment, the check in step S23 can be omitted. The operation of apparatuses composing the dynamic image diagnostic assistance system 100 is the same as that described in the first embodiment and the description is incorporated herein.

The bone extracting process according to the second embodiment is performed by the following steps (a) and (b). First, in step (a), a complete bone extraction process is separately applied to each frame image to only the first k frame images (k=1 to a few frames) among the collected dynamic images (first extraction). The complete bone extraction process is the bone extraction process described in step S22 shown in FIG. 3. Preferably, when k>1, as described above, the bone extraction process result of the first k frame images are checked, and each of the bone extraction result of the first k frame images are corrected.

In step (b), the bone extraction process on the frame images from k+1-th frame image and after, the bone extraction process is performed by a simple image process on the basis of the bone extraction result of k-frame images (second extraction).

For example, in the simple bone extraction process, the bone candidate region is extracted by searching the spatial edge (inclination) of the bone in only a few pixels near a bone region boundary based on the bone region extracted in the frame image directly before. With this, the amount of calculation in the process can be reduced and processing at a high speed becomes possible. As one example of a method to accurately extract the spatial edge of the bone, there is a method using the dynamic outline extraction. The coordinates of the bone region extracted from the frame image directly before is to be the initial position. The shape of the bone and the edge features in the image is to be the evaluation function. With this, the outline extraction is performed a plurality of times. Consequently, the outline of the bone can be recognized accurately. By using such dynamic outline extraction, such method can adapt to change in the shape and position of the target bone, and therefore, this method can be used in images with great change among the frame images. For example, the method is effective when the above bone reduction process is applied to two or more frame images captured with a certain period or more in between, the difference among the frame images after bone reduction is obtained and the difference is extracted.

The following process is possible for easier processing. For example, when the captured image is dynamic images showing the breathing state of the thoracic portion, the ribs and the clavicles move upward in inhaling and downward in exhaling. Therefore, it is determined whether it is the timing of inhaling or exhaling in each frame image, and the edge is searched in the bone region extracted in the frame image directly before only in the upward direction when the timing is inhaling and only in the downward direction when the timing is exhaling.

It is possible to determine whether it is the timing of inhaling or exhaling, by judging the direction that the diaphragm moved from the frame image directly before or whether the density change in the lung field region increased or decreased from the frame image directly before. When the moving direction of the diaphragm is judged, it is possible to determine that it is the inhaling when the diaphragm moves downward and it is the exhaling when the diaphragm moves upward. When the density change in the lung field region is judged, it is possible to determine that it is the inhaling when the density increases and exhaling when the density decreases. The density inclination of the diaphragm is large. Therefore, by detecting the edge of the diaphragm, it is possible to easily understand whether the frame image is inhaling or exhaling. The lung field region can be identified by detecting the edge of the rib cage. However, even if the lung field region is not identified, the inhaling and exhaling timing can be determined by whether the density of the fixed region in the center of the image is increasing or decreasing.

In the thoracic dynamic images, each frame image is an image with low irradiating amount and large noise. Therefore, the first k frame images can be overlapped and combined, and the complete bone extraction process can be applied to the combined image. Then, based on the obtained bone extraction result, the bone extraction is performed on the first frame image with the simple image process. The frame images thereafter are processed with the bone extraction process using the simple image process based on the bone extraction result of the frame image directly before.

As described above, the frame images are sequentially processed referring to the bone extraction result of the frame image directly before. Consequently, it is possible to prevent the bone extraction result from being different in a certain region among the adjacent frame images before and after the target frame image. The bone extraction process of each frame image is simplified to increase the processing speed of the bone extraction process. By increasing the processing speed of the bone extraction process, the interval of time of capturing the frame image, applying the bone reduction in the frame image, and displaying or applying the analysis process on the dynamic images after bone reduction can be shortened. With this, the feature of real-time output of the image to the user can be enhanced.

The first and second embodiments are described above, but the embodiments described above are preferable examples of the present invention. The present invention is not limited to the above.

For example, the processes performed in the embodiments are performed in the unit of pixels, but the processes can be performed in a unit of small regions including a plurality of pixels.

For example, according to the above-described embodiments, the capturing site is the thoracic portion, but other sites can be captured. According to the above-described embodiments, the reduced structures are the ribs, and the clavicles. The structures are not limited to the above and for example, other bones such as shoulder blades, or vertebrae, or blood vessels can be reduced.

According to the bone reduction process in the present embodiment, reducing the spatial signal change due to the structure is described in the thoracic dynamic images. The above bone reduction process can be applied to reduction of the spatial signal change due to structures in a group of images including the present X-ray image and the past X-ray image which are captured by irradiating the X-rays with substantially the same energy, that is, substantially the same tubular voltage to the same site of the same subject with a certain amount of time or more in between.

The above-described embodiment describes an X-ray image obtained by a radiation detector such as a FPD. Alternatively, the present invention can be applied to a CT image, a scintigraphy image, or a PET image.

According to the above-described embodiment, the capturing console 2 and the diagnostic console 3 are connected through a network. Alternatively, the capturing console 2 and the diagnostic console 3 can be formed as one, and the capturing console 2 can include the function of the diagnostic console 3. Alternatively, the diagnostic console 3 may be a configuration in a far and separated place from the capturing console 2, for example, a resource on a cloud.

According to the above description, a hard disk or a semiconductor nonvolatile memory is used as the computer-readable medium storing the program, but the present invention is not limited to the above. A portable recording medium such as a CD-ROM can be applied as the computer-readable medium. A carrier wave can be applied as the medium to provide the data of the program of the present invention through communication lines.

The present invention is not limited to the above embodiment, and the detailed structure and the detailed operation of each apparatus composing the dynamic image diagnostic assistance system 100 of the present invention can be suitably changed without leaving the scope of the present invention.

The present U.S. patent application is related to Japanese Patent Application No. 2014-206125 filed on Oct. 7, 2014 the entirety of which is incorporated herein by reference.

What is claimed is:

1. An image processing apparatus comprising:
   a structure reducing unit which reduces spatial signal change by a predetermined structure in an X-ray image group in which a plurality of images obtained by irradiating a plurality of X-rays to a same site of a same subject are sequentially aligned,
   wherein the structure reducing unit includes:
   an extracting unit which obtains an extraction result by extracting a region of the predetermined structure from each image of the X-ray image group;
   a comparing unit which obtains a compared result by comparing the extraction result for each image of the X-ray image group with the extraction result of a different image of the X-ray image group that is different from the each image, and which corrects the extraction result of the each image based on the compared result; and
   a reducing unit which specifies the region of the predetermined structure of the each image of the X-ray image group based on the extraction result after processing by the comparing unit and reduces the spatial signal change in the region.

2. The image processing apparatus according to claim 1, further comprising:
   a re-extracting unit which extracts the region of the predetermined structure again from the image on which correction of the extraction result by the extracting unit is performed by the comparing unit based on the corrected extraction result.

3. The image processing apparatus according to claim 1, wherein the comparing unit compares the extraction result by the extracting unit for each image of the X-ray image group with the extraction result of a plurality of images of the X-ray image group successive in a time series with the image.

4. The image processing apparatus according to claim 3, wherein, for each pixel or each small region including a plurality of pixels in each image of the X-ray image group, the comparing unit determines whether the pixel or the small region is extracted as the region of the predetermined structure in the image and a predetermined number or more images among a plurality of images successive to the image in a time series, and when a determination result is different from the extraction result in the pixel or the small region of the image, the extraction result in the pixel or the small region of the image is corrected to a result which is the same as the determination result.

5. The image processing apparatus according to claim 3, wherein, in each image of the X-ray image group, the comparing unit assigns a predetermined value in the pixel or small region extracted as the region of the predetermined structure by the extracting unit, assigns 0 to a pixel or a small region which is not extracted as the region of the predetermined structure by the extracting unit, adds the numerals assigned to the image and the plurality of images successive in a time series to the image for each pixel or small region in the image, determines the pixel or the small region in which an added result is a predetermined threshold or more as the region of the predetermined structure, and when the determined result is different from the extraction result in the pixel or the small region of the image, the extraction result of the pixel or the small region of the image is corrected to a result which is the same as the determination result.

6. The image processing apparatus according to claim 5, wherein, when the comparing unit adds the values assigned to the image and the plurality of images successive in a time series to the image for each pixel or each small region including a plurality of pixels in each image, the comparing unit applies a weighting coefficient to each of the image and the plurality of images successive to the image, and the comparing unit determines that the pixel or the small region is the region of the predetermined structure when a result of adding values of a result of multiplying the applied weighting coefficient to the assigned value is the predetermined threshold or more.

7. The image processing apparatus according to claim 6, wherein the site of the subject of the X-ray image group is a thoracic portion, the image processing apparatus further comprises an acknowledging unit which acknowledges a breathing phase in each image of the X-ray image group, and the comparing unit changes a weighting coefficient assigned to a target image of comparison and the image used in comparison with the target image based on the breathing phase of the target image of comparison.

8. The image processing apparatus according to claim 1, wherein the site of the subject of the X-ray image group is a thoracic portion, the image processing apparatus further comprises an acknowledging unit which acknowledges a breathing phase in each image of the X-ray image group, and the comparing unit changes a number of images used in comparison with a target image based on the breathing phase of the target image of comparison.

9. An image processing apparatus comprising:

a structure reducing unit which reduces spatial signal change by a predetermined structure in an X-ray image group in which a plurality of images obtained by irradiating a plurality of X-rays to a same site of a same subject are sequentially aligned, wherein the structure reducing unit further includes, a first extracting unit which extracts a region of the predetermined structure from any one or more images of the X-ray image group;

a second extracting unit which refers to the region of the predetermined structure extracted by the first extracting unit and extracts a region of the predetermined structure from another image of the X-ray image group which is not a target of extraction by the first extracting unit; and a reducing unit which specifies a region of the predetermined structure from each image of the X-ray image group based on an extraction result of the region of the predetermined structure and reduces a spatial signal change in the region.

10. An image processing apparatus comprising:

a structure reducing unit which reduces spatial signal change by a predetermined structure in an X-ray image group in which a plurality of images obtained by irradiating a plurality of X-rays to a same site of a same subject are sequentially aligned, wherein the structure reducing unit compares a result of reduction of the spatial signal change of the predetermined structure in each image of the X-ray image group with a result of reduction of an image different from the image of the X-ray image group after a process of reduction of the spatial signal change of the predetermined structure in each image of the X-ray image group, and as a result of comparison, when a degree of reduction of the spatial signal change in the predetermined structure is low compared to the different image, the process of reduction of the spatial signal change of the predetermined structure in the image is performed again.

11. An image processing apparatus comprising:

a structure reducing unit which reduces spatial signal change by a predetermined structure in an X-ray image group in which a plurality of images obtained by irradiating a plurality of X-rays to a same site of a same subject are sequentially aligned, wherein the structure reducing unit further includes, a density profile creating unit which creates a density profile of the predetermined structure used to reduce the spatial signal change of the predetermined structure in the image for each image of the X-ray image group; and a density profile correcting unit which corrects the density profile created for each image before performing a process of reduction using the density profile on the basis of the density profile of the image and the density profile of at least one image different from the image.

12. The image processing apparatus according to claim 11, wherein, the density profile correcting unit corrects the density profile created for each image on the basis of a density profile of the image and density profiles of images time-sequentially before and after the image.

13. The image processing apparatus according to claim 12, wherein the density profile correcting unit corrects the density profile created for each image on the basis of the density profile of the image and a central value of the density profiles of the images time-sequentially before and after the image.

14. The image processing apparatus according to claim 1, wherein the X-ray image group is a plurality of frame images showing a moving state of the site of the subject.

15. The image processing apparatus according to claim 1, wherein the X-ray image group includes at least two or more images capturing the same site of the same subject over a certain period of time or more.

16. A non-transitory computer-readable recording medium having a program stored thereon for controlling a computer used in an image processing apparatus which reduces spatial signal change by a predetermined structure in an X-ray image group in which a plurality of images obtained by irradiating a plurality of X-rays to a same site of a same subject are time-sequentially aligned, wherein the program controls the computer to function as:

an extracting unit which extracts a region of the predetermined structure from each image of the X-ray image group;

a comparing unit which compares an extraction result by the extracting unit for each image of the X-ray image group with an extraction result of the image different from the image of the X-ray image group, and which corrects the extraction result of the image based on a compared result; and a reducing unit which specifies a region of the predetermined structure from each image of the X-ray image group based on the extraction result after processing by the comparing unit and reduces the spatial signal change in the region.

17. The image processing apparatus according to claim 3, wherein the plurality of images of the X-ray image group successive in a time series include an image captured before the image and an image captured after the image.

18. The image processing apparatus according to claim 1, wherein the predetermined structure is a bone of the subject.

* * * * *